(12) United States Patent
Datla et al.

(10) Patent No.: US 11,718,640 B2
(45) Date of Patent: Aug. 8, 2023

(54) PROCESS FOR EXTRACTION OF CHOLESTEROL FROM FISH OIL WASTE RESIDUE

(71) Applicant: FERMENTA BIOTECH LIMITED, Thane (IN)

(72) Inventors: Anupama Datla, Mumbai (IN); Prashant Nagre, Thane West (IN); Jagdish Tamore, Thane West (IN); Sreenath Trivikram, Dombivili (IN); Gajanan Degaonkar, Badlapur (IN)

(73) Assignee: FERMENTA BIOTECH LIMITED, Thane (IN)

( * ) Notice: Subject to any disclaimer, the term of this patent is extended or adjusted under 35 U.S.C. 154(b) by 440 days.

(21) Appl. No.: 16/629,487

(22) PCT Filed: Sep. 12, 2018

(86) PCT No.: PCT/IN2018/050592
§ 371 (c)(1),
(2) Date: Jan. 8, 2020

(87) PCT Pub. No.: WO2019/053744
PCT Pub. Date: Mar. 21, 2019

(65) Prior Publication Data
US 2021/0139527 A1    May 13, 2021

(30) Foreign Application Priority Data
Sep. 14, 2017    (IN) .............................. 201721032632

(51) Int. Cl.
*C07J 9/00*    (2006.01)
*C07C 29/56*    (2006.01)

(52) U.S. Cl.
CPC ................. *C07J 9/00* (2013.01); *C07C 29/56* (2013.01)

(58) Field of Classification Search
CPC .. C07J 9/00; C07C 29/56; C11C 1/025; C11C 1/08
See application file for complete search history.

(56) References Cited

U.S. PATENT DOCUMENTS

2011/0207952 A1*    8/2011    Avila .......................... C07J 9/00
552/545

FOREIGN PATENT DOCUMENTS

| CN | 107141331 | * | 9/2017 |
| EP | 0 255 824 | | 1/1990 |
| GB | 1164769 | * | 9/1969 |
| WO | 2016/096989 A1 | | 6/2016 |

OTHER PUBLICATIONS

Morrison and Boyd, 3rd Edition, p. 688, (Year: 1976).*
International Search Report dated Dec. 13, 2018 in connection with International Application No. PCT/IN2018/050592.

* cited by examiner

*Primary Examiner* — Barbara P Badio
(74) *Attorney, Agent, or Firm* — Kramer & Amado, P.C.

(57) ABSTRACT

The present invention discloses an improved process for extracting cholesterol in high yield and purity from fish oil waste residue. The so obtained cholesterol of pharmaceutical grade is useful as a precursor for the preparation of vitamin D3.

9 Claims, No Drawings

PROCESS FOR EXTRACTION OF CHOLESTEROL FROM FISH OIL WASTE RESIDUE

FIELD OF INVENTION

The present invention relates to improved process for extracting cholesterol in high yield and purity from fish oil waste residue. The so obtained cholesterol of pharmaceutical grade is useful as a precursor for the preparation of vitamin D3.

BACKGROUND OF THE INVENTION

Cholesterol, having 1UPAC name (3β)-cholest-5-en-3-ol and which systematic name is 2,15-dimethyl-14-(1,5-dimethylhexyl)tetracyclo[8.7.0.02'7.011'15]heptacos-7-en-5-ol a waxy substance found in some foods and manufactured in the body, it serves as a precursor for the biosynthesis of steroid hormones, bile and vitamin D.

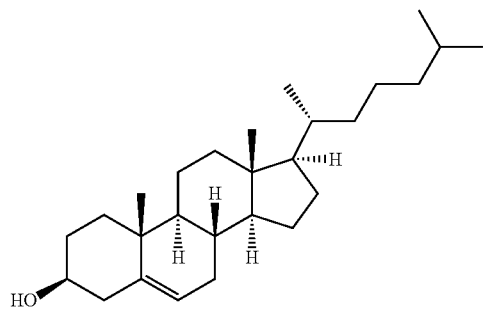

Cholesterol can be found in egg yolk, organ meat, shrimp, squid, beef, pork, poultry, fish, wool grease, full-fat dairy products, butter, hard margarines, lard, coconut oil, ghee (clarified butter), vegetable ghee, palm oil. These sources usually contain cholesterol in its free form as well as in the esterified form. The most important source of cholesterol is lanolin, which is obtained from the wool of sheep. However, since the composition of fatty acids in wool grease is of complex nature due to the presence of free acids and alcohols which can form varied esters, the extraction of cholesterol is cumbersome and costly.

The crude fish oils primarily contain triglycerides which represent about 90% of the composition. The other balance components comprises partial glycerides (i.e. mono or diglycerides), free fatty acids, phospholipids and group of chemicals as un-saponifiable fraction which include cholesterol-sterol, glyceryl ethers, fatty alcohols, vitamins and oxidised pigments. The content of the un-saponifiable fraction varies with seasonal and feeding conditions and varies in the range of 2-8%.

The fish oil waste residue from the fish refining industry contains useful products such as cholesterol, proteins and enzymes among other fatty acids. Due to the importance of cholesterol as precursor in the manufacturing of vitamin D3, the fish oil and fish oil residue (after removing polyunsaturated fatty acids) which form the waste stream in the fish oil industry are now considered as an alternative source of cholesterol.

EP0255824 discloses a process for production of a refined fish oil concentrate containing at least 20% eicosapentaenoic acid (EPA) and at least 35% docosehexaensoic acid (DHA) by weight, cholesterol and useful byproducts. The process disclosed in EP'824 is specifically related to obtain refined fish oil concentrate and cholesterol is separated as by product. Urea is used in EP' 824 to form adduct of fatty acid alkyl ester which is precipitated out and cholesterol which do not form an adduct with urea is crystallized out from the filtrate using solvent.

WO2016096989 disclose a process for extracting cholesterol from fish oil by saponification in presence of NaOH/KOH followed by extraction with at least one non-water miscible solvent such as aliphatic or aromatic hydrocarbon at temperature above 30° C. The process involves repeated solvent extractions, crystallization and back washes to extract cholesterol. The process described in WO'989 is multistep cumbersome solvent extraction process that requires large volume of solvents. The total yields (w/w w.r.t. fish oil) and purity are low.

In view of the above, the present inventors have developed an improved process for the extraction of cholesterol from fish oil waste residue enriched in cholesterol (both free and esterified form) in high yield and purity.

SUMMARY OF THE INVENTION

In accordance with the above, the present invention provides an improved process for extraction of cholesterol in high yield and purity from fish oil waste product which comprises;
  i. saponifying the fish oil waste residue in presence of 4-dimethylaminopyridine as catalyst followed by neutralization with aqueous acid to obtain ester free cholesterol;
  ii. heating the saponified mass in 2-butanone, after phase separation, at elevated temperature with calcium bromide to obtain cholesterol-adduct; and
  iii. separating cholesterol from the adduct followed by re-crystallization from methanol to yield pure cholesterol.

In an aspect, the ratio of sterol containing mass to calcium bromide is in the range of 1:1 to 1:10, preferably 1:1 to 1:5 and more preferably 1:1.

In an aspect, cholesterol obtained by the process of present invention is highly pure with HPLC purity in the range of 95-97% and can be used as a precursor for manufacture of vitamin D3.

DETAILED DESCRIPTION OF THE INVENTION

Source of biological material: The fish oil waste product is obtained from fish oils extracted from varieties of Fishes containing polyunsaturated fatty acids (PUFA's) and cholesterol.

The fish oils mainly contain polyunsaturated fatty acids (PUFA's) which are valuable nutraceuticals, partial glycerides (i.e. mono or diglycerides), phospholipids and only about 1-3% cholesterol. The PUFA's are extracted from the fish oil by known methods such as extraction, distillation etc. The residue after removal of PUFA is a fish oil waste residue containing 5-50% cholesterol depending on the weight of the fish oil waste residue either in its free form or as ester and high boiling fractions of fish oil. The fish oil waste residue is usually discarded or burnt.

The present inventors therefore felt that the fish oil waste residue enriched with cholesterol can serve as potential raw material for extraction of cholesterol which is an important precursor in biotransformation reactions. To meet the industrial requirements of cholesterol production of pharmaceutical grade and expand the raw material base, the present invention provides an improved process for extraction of cholesterol in high yield and purity from fish oil waste product enriched in cholesterol (both free and esterified form) obtained after molecular distillation of fish oil.

In an embodiment, the improved process for extraction of cholesterol in high yield and purity from fish oil waste residue is characterized by process steps which comprises;
  i. saponifying the fish oil waste product in presence of 4-dimethylaminopyridine as catalyst followed by neutralization with aqueous acid to obtain ester free cholesterol;
  ii. heating the saponified mass in 2-butanone, after phase separation, at elevated temperature with calcium bromide to obtain cholesterol-adduct; and
  iii. separating cholesterol from the adduct followed by re-crystallization from methanol to yield pure cholesterol.

Accordingly, the fish oil waste product containing cholesterol (free and esterified) in the range of 0.4-0.6 gms per gm of fish oil waste product was subjected to saponification in alkaline base such as sodium hydroxide in presence of 4-dimethylamino pyridine as catalyst in an amount of 0.5-50 gms. The saponification was carried out in lower alcohol such as methanol. The mixture was refluxed for about 0.5-6 hours. After about an hour the solvent was distilled out by raising the temperature to 70-80° C.

The mixture was neutralized at same temperature using 20-25% sulphuric acid. Water was added followed by addition of 2-butanone and the reaction mass was stirred for 10-90 minutes at 50-80° C. The organic and aqueous layers were separated. The omega acids and all other residual acids/impurities were washed away in the aqueous layer and the mother liquor was further washed with saturated salt solution to remove any traces of water. The organic solvent was evaporated by heating at temperature of 90-95° C. 2-butanone was further added at same temperature and the reaction mass containing sterol was cooled to 65-70° C.

In an embodiment of the present process, the ester free sterol adduct was obtained by heating the above cooled reaction mass with inorganic salt selected from alkali or alkaline earth metals halides, nitrates, sulfates, preferably halides such as calcium bromide in an amount of 50-500 gms. The temperature was maintained in the range of 25-80° C., preferably at 40-80° C. more preferably at 60-75° C. for 7-16 hours. After about 8 hours of heating the reaction mass was cooled to about 30° C., filtered, washed with 2-butanone. The solid residue containing sterol was further suspended in methanol and refluxed for 3-4 hours, cooled to 35° C., maintained at same temperature for another 3-4 hours, filtered and washed with methanol remove the inorganic salt.

The salt free solid residue was further suspended in aliphatic or aromatic hydrocarbon such as hexane, heptane, toluene, xylene, ethyl toluene and the like; preferably toluene and the mixture was heated to a temperature in the range of 40-50° C. to remove any further impurities. The suspension was filtered and washed with Toluene. The residual solid was rejected and the entire filtrate i.e. organic layer containing cholesterol was evaporated under vacuum at 60-70° C. and was further treated with methanol to remove the residual toluene. The crude cholesterol was further purified by adding methanol and heating the reaction mixture at 60-70° C. for 1-5 hours. The reaction mass was cooled to 30-35° C. and maintained for 2-6 hours, the solid was filtered, washed, dried under vacuum to obtain pure cholesterol.

In an embodiment, the ratio of sterol to calcium bromide is in the range of 1:1 to 1:10, preferably 1:1 to 1:5 and more preferably 1:1.

The use of 4-dimethylamino pyridine as catalyst in the saponification reaction of the present invention enhances hydrolysis of the esterified group in the cholesterol resulting in free sterol. The reaction can be performed in less time and at temperature which is not higher than the boiling point of the solvent used.

The inorganic salt such as calcium bromide selectively forms adduct with cholesterol which can be easily separated out from the solvent. The reaction was carried out at elevated temperature which shortens the duration time of the reaction. The adduct formation in the present process reduces the excess use of solvents for extraction of cholesterol as employed in prior art processes. The present process is thus cost effective and industrially viable.

In an embodiment, cholesterol extracted from fish oil waste product by the process of the present invention is characterized by HPLC purity in the range of 95-97%.

In another embodiment, cholesterol obtained by the present process can be used as precursor for manufacture of vitamin D, preferably D3 via 25-hydroxy cholesterol by a process known in the art.

In yet another embodiment, the residue after the extraction of cholesterol is used as biofuel.

In the advantageous embodiment, the present invention provides for extraction of cholesterol in high yield and purity from an alternate source such as fish oil waste residue enriched in cholesterol (both free and esterified form) in a simple and cost effective manner.

The example herein is provided to illustrate particular aspect of the disclosure and do not limit the scope of the present invention.

Example 1: Cholesterol from Fish Oil 400 gms of Fish oil waste product (containing 0.4-0.6 gm cholesterol (free and ester form) per gm of fish oil waste product) was suspended in 400 ml of methanol. 40 gms of sodium hydroxide and 1 gm of 4-dimethylamino pyridine were added and the reaction mass was refluxed for 1 hour. After 1 hour, methanol was distilled at 70-75° C. At 75° C. 600 ml of 25% sulphuric acid and 300 ml of water were added. 600 ml of 2-butanone was added and the reaction mass was stirred for 30 minutes at 75° C. The organic and the aqueous layers were separated. The organic layer was washed with 3×100 ml of saturated salt solution. 2-butanone was evaporated at 90-95° C.

Further, 800 ml of 2-butanone was added to the above reaction mass, cooled to 65-70° C. 190 gms of calcium bromide was added and the reaction was heated at 65-70° C. for 8 hours. The reaction was cooled to 30° C., filtered, washed with 100 ml of 2-butanone. The solid residue was suspended in 600 ml of methanol, refluxed for 3 hours. The reaction mas was cooled to 35° C., maintained at same temperature for 3 hours, filtered and washed with 150 ml methanol.

The solid residue was suspended in 1080 ml toluene and heated to 45-50° C., Filtered and washed with 100 ml Toluene. The entire filtrate i.e. Toluene layer containing cholesterol was evaporated under vacuum at 65-70° C. The residue was treated with 100 ml of methanol to remove residual toluene. 400 ml of methanol was further added and heated to 65° C., maintained at same temperature for 2 hours. Cooled the reaction mass to 30-35° C. and maintained for 2 hours. The solids were filtered and washed with 100 ml methanol. The isolated solids were dried under vacuum at 65-70° C. to yield cholesterol of high purity determined by HPLC.

Yield: 200-220 gms
% Yields (w/w w.r.t.fish oil waste product): ≥50%
HPLC purity: 95%

It is to be understood that the above description is intended to be illustrative and not restrictive. Many embodiments will be apparent to a person skilled in the art upon reviewing the description. The scope of the invention should therefore, be determined not with reference to the above description, but instead should be determined with reference to the appended claims, along with the full scope of equivalents to which such claims are entitled.

We claim:

1. A process for extraction of cholesterol from fish oil waste residue enriched in cholesterol, comprising:
   i. saponifying the fish oil waste residue in the presence of a base and 4-dimethylaminopyridine, wherein 4-dimethylaminopyridine is a catalyst, to produce a saponified residue;
   ii. neutralizing the saponified residue with aqueous acid to produce a saponified mass containing ester-free cholesterol;
   iii. heating a mixture of the saponified mass and 2-butanone at an elevated temperature of 25° C. to 80° C. in the presence of calcium bromide to obtain a cholesterol-calcium adduct; and
   iv. separating cholesterol from the cholesterol-calcium adduct.

2. The process according to claim 1, wherein the heating step comprises heating the mixture of the saponified mass and 2-butanone, wherein a ratio of the ester-free cholesterol to the calcium bromide is between 1:1 and 1:10.

3. The process according to claim 2, wherein the ratio of the ester-free cholesterol to the calcium bromide is 1:1.

4. The process according to claim 1, wherein the step of separating cholesterol from the cholesterol-calcium adduct comprises heating the cholesterol-calcium adduct in refluxing methanol.

5. The process according to claim 1, wherein the heating step comprises heating the mixture of the saponified mass and 2-butanone to a temperature of between 40° C. and 80° C.

6. The process according to claim 5, wherein the heating step comprises heating the mixture of the saponified mass and 2-butanone to a temperature of between 65° C. and 70° C.

7. The process according to claim 1, wherein the separating step comprises separating cholesterol from the cholesterol-calcium adduct to produce cholesterol which is between 95% and 97% pure.

8. A process for preparing vitamin D3, comprising:
   i. extracting cholesterol from fish oil waste residue by the process of claim 1;
   ii. converting the extracted cholesterol into 25-hydroxycholesterol; and
   iii. converting the 25-hydroxycholesterol into vitamin D3.

9. A process for extraction of cholesterol from fish oil waste residue enriched in cholesterol, comprising:
   i. saponifying the fish oil waste residue to produce a saponified residue, the saponifying being carried out in the presence of:
      a hydroxide base, and
      a 4-dimethylaminopyridine catalyst;
   ii. neutralizing the saponified residue with aqueous acid to produce a saponified mass containing ester-free cholesterol;
   iii. heating a mixture of the saponified mass and 2-butanone at an elevated temperature of 25° C. to 80° C. in the presence of calcium bromide to obtain a cholesterol-calcium adduct; and
   iv. separating cholesterol from the cholesterol-calcium adduct.

* * * * *